(12) United States Patent
Meldrum et al.

(10) Patent No.: US 10,221,443 B2
(45) Date of Patent: Mar. 5, 2019

(54) SYSTEM AND METHOD FOR LASER LYSIS

(71) Applicant: ARIZONA BOARD OF REGENTS ON BEHALF OF ARIZONA STATE UNIVERSITY, Scottsdale, AZ (US)

(72) Inventors: Deirdre Meldrum, Phoenix, AZ (US); Shih-Hui (Joseph) Chao, Phoenix, AZ (US); Thai Tran, Phoenix, AZ (US); Laimonas Kelbauskas, Gilbert, AZ (US); Jeff Houkal, Los Angeles, CA (US); Andrew Hatch, Tempe, AZ (US); Weimin Gao, Chandler, AZ (US); David Richardson, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 77 days.

(21) Appl. No.: 15/135,150

(22) Filed: Apr. 21, 2016

(65) Prior Publication Data
US 2016/0237476 A1    Aug. 18, 2016

Related U.S. Application Data

(62) Division of application No. 14/909,195, filed as application No. PCT/US2014/056960 on Sep. 23, 2014.

(Continued)

(51) Int. Cl.
*C12Q 1/68* (2018.01)
*C12Q 1/6806* (2018.01)
(Continued)

(52) U.S. Cl.
CPC .......... *C12Q 1/6806* (2013.01); *B01L 3/0293* (2013.01); *B01L 3/502761* (2013.01);
(Continued)

(58) Field of Classification Search
CPC ........................................................ C12Q 1/68
See application file for complete search history.

(56) References Cited

U.S. PATENT DOCUMENTS 6,156,576 A    12/2000   Allbritton et al.
6,514,481 B1   2/2003    Prasad et al.
(Continued)

FOREIGN PATENT DOCUMENTS

WO    2012162779 A1    12/2012
WO    2015048009 A1    4/2015

OTHER PUBLICATIONS

White et al. (High-throughput microfluidic single-cell digital polymerase chain reaction, Anal Chem. Aug. 6, 2013;85(15):7182-90. Epub Jul. 24, 2013).*

(Continued)

*Primary Examiner* — Aaron A Priest
(74) *Attorney, Agent, or Firm* — Gavin J. Milczarek-Desai; Quarles & Brady LLP

(57) ABSTRACT

Systems and methods for in situ laser lysis for analysis of biological tissue (live, fixed, frozen or otherwise preserved) at single cell resolution in 3D. For example, a system and method for lysing individual cells in situ, including the steps of capturing a tissue sample comprising a cellular content, subjecting the tissue sample to a stream of continuous fluid flow, lysing a selected area of the tissue sample with a laser, thereby releasing at least a portion of the cellular content from the tissue sample, recovering at least one target molecule from the cellular content in the stream, and processing at least one target molecule is provided. The system collects cellular contents, performs highly multiplexed (RT-qPCR or RNA-seq), and sequentially (cell-by-cell) reconstructs a 3D spatial map of mRNA expression of the tissue with a large (Continued)

number of genes. A 3D spatial map of the DNA, RNA, and/or proteins can be generated for each cell in the tissue.

5 Claims, 13 Drawing Sheets

Related U.S. Application Data

(60) Provisional application No. 61/883,739, filed on Sep. 27, 2013.

(51) Int. Cl.
    *C12M 1/00*     (2006.01)
    *G01N 1/28*     (2006.01)
    *C12Q 1/6848*     (2018.01)
    *B01L 3/02*     (2006.01)
    *B01L 3/00*     (2006.01)
    *C12Q 1/6841*     (2018.01)
    *C12Q 1/686*     (2018.01)

(52) U.S. Cl.
    CPC .............. *C12M 47/06* (2013.01); *C12Q 1/686* (2013.01); *C12Q 1/6841* (2013.01); *C12Q 1/6848* (2013.01); *G01N 1/286* (2013.01); *B01L 2200/0668* (2013.01); *B01L 2300/0816* (2013.01); *B01L 2300/0829* (2013.01); *B01L 2300/0864* (2013.01); *G01N 2001/2886* (2013.01)

(56) References Cited

U.S. PATENT DOCUMENTS

| | | | |
|---|---|---|---|
| 6,815,209 B2 | 11/2004 | Baeummer et al. | |
| 7,531,138 B2 | 5/2009 | Kim et al. | |
| 7,613,571 B2* | 11/2009 | Doyle .................. | C12Q 1/6841 435/6.14 |
| 7,855,069 B2 | 12/2010 | Lee et al. | |
| 7,892,491 B2 | 2/2011 | Kim et al. | |
| 7,910,343 B2 | 3/2011 | Kim et al. | |
| 7,955,801 B2 | 6/2011 | Lee et al. | |
| 7,959,862 B2 | 6/2011 | Cho et al. | |
| 8,232,094 B2 | 7/2012 | Hasson et al. | |
| 8,252,569 B2 | 8/2012 | Cho et al. | |
| 8,658,359 B2 | 2/2014 | Lee et al. | |
| 2007/0134809 A1 | 6/2007 | Cho et al. | |
| 2008/0125330 A1 | 5/2008 | Cady et al. | |
| 2008/0199930 A1 | 8/2008 | Lee et al. | |
| 2008/0318279 A1 | 12/2008 | Lee et al. | |
| 2009/0215023 A1 | 8/2009 | West et al. | |
| 2010/0028980 A1 | 2/2010 | Hasson et al. | |
| 2011/0143414 A1 | 6/2011 | Cho et al. | |
| 2011/0312808 A1 | 12/2011 | Azimi et al. | |

OTHER PUBLICATIONS

Brown et al. (Current techniques for single-cell lysis, J R Soc Interface. Oct. 6, 2008; 5(Suppl 2): S131-S138).*
Rau et al. (Pulsed laser microbeam-induced cell lysis: time-resolved imaging and analysis of hydrodynamic effects, Biophys J. Jul. 1, 2006;91(1):317-29. Epub Apr. 14, 2006).*
Zhang et al., Microfluidic DNA amplification—A review., Analytica Chimica Acta, 2009, 638(2)115-125.
Lai et al., Characterization and use of laser-based lysis for cell analysis on-chip., Journal of the Royal Society Interface, Oct. 2008, 5(supp. 2):S113-S121.
Markey et al., High-throughput droplet PCR., Methods, 2010, 50(4):277-281.
Brown et al., Current techniques for single-cell lysis., Journal of the Royal Society Interface, Oct. 2008, 5(supp. 2):S131-S138.
Chao et al., Microfluidic devices for high-throughput proteome analyses., Proteomics, Feb. 2013, 13(3-4):467-479.
Evstrapov, Microfluidic chips for biological and medical research., Russian Journal of General Chemistry, Dec. 2012, 82(12):2132-2145.
Hung et al., An integrated microfluidic platform for rapid tumor cell isolation, counting and molecular diagnosis., Biomedical Microdevices, Apr. 2013, 15(2):339-352.
Saunders et al., Rapid, quantitative, reverse transcription PCR in a polymer microfluidic chip., Biosensors & Bioelectronics, Jun. 2013, 44:222-228.
Zeng et al., Quantitative microfluidic biomolecular analysis for systems biology and medicine., Analytical and Bioanalytical Chemistry, Jul. 2013, 405(17):5743-5758.
Dhawan et al., Development of a laser-induced cell lysis system., Analytical and Bioanalytical Chemistry, Oct. 2002, 374(3):421-426.
Juncker et al., Autonomous microfluidic capillary system., Analytical Chemistry, Dec. 2002, 74(24): 6139-6144.
Zhang et al., Cancer-stromal interactions: Role in cell survival, metabolism and drug sensitivity., Cancer Biology & Therapy, Jan. 2011, 11:150-156.
Calorini et al., Environmental control of invasiveness and metastatic dissemination of tumor cells: the role of tumor cell-host cell interactions., Cell Communication and Signaling, 2010, 8:24.
Citri et al., Comprehensive qPCR profiling of gene expression in single neuronal cells., Nature Protocols, 2012, 7(1):118-127.
Guo et al., Resolution of Cell Fate Decisions Revealed by Single-Cell Gene Expression Analysis from Zygote to Blastocyst, Developmental Cell, Apr. 2010, 18(4):675-685.
Sarkar et al., Microfluidic probe for single-cell analysis in adherent tissue culture., Nature Communications, Mar. 2014, 5:3421.
Heisterkamp et al., Pulse energy dependence of subcellular dissection by femtosecond laser pulses., Optics Express, May 2005, 13(10):3690-3696.
Quinto-Su, Examination of laser microbeam cell lysis in a PDMS microfluidic channel using time-resolved imaging., Lab on a Chip, 2008, 8(3):408-414.
Rau et al., Pulsed Laser Microbeam-Induced Cell Lysis: Time-Resolved Imaging and Analysis of Hydrodynamic Effects., Biophysical Journal, 2006, 91(1):317-329.
Rau et al., Investigation of laser-induced cell lysis using time-resolved imaging., Applied Physics Letters, Apr. 2004, 84(15):2940-2942.
Sims et al., Laser-micropipet combination for single-cell analysis., Analytical Chemistry, Nov. 1998, 70(21):4570-4577.
Li et al., Spatial control of cellular measurements with the laser micropipet, Analytical Chemistry, Oct. 2001, 73(19):4625-4631.
Anis et al., Automated Selection and Placement of Single Cells Using Vision-Based Feedback Control., IEEE Transactions on Automation Science and Engineering, 2010, 7(3):598-606.
Anis et al., Diaphragm pico-liter pump for single-cell manipulation., Biomedical Microdevices, Aug. 2011, 13(4):651-659.
Yamanaka et al., Rapid detection for primary screening of influenza A virus: Microfluidic RT-PCR chip and electrochemical DNA sensor., Analyst, May 2011, 136(10):2064-2068.
Zhou et al., Recent developments in PDMS surface modification for microfluidic devices., Electrophoresis, Jan. 2010, 31(1):2-16.
White et al., High-throughput microfluidic single-cell RT-qPCR., Proceedings of the National Academy of Sciences of the United States of America, Aug. 2011, 108(34):13999-14004.
Witte et al., Continuous cell lysis in microfluidics through acoustic and optoelectronic tweezers., Proceedings of SPIE—The International Society for Optical Engineering, 2013, 8615:86150T.
Velve-Casquillas et al., Microfluidic tools for cell biological research., Nano Today, 2010, 5(1):28-47.
Sanchez-Freire et al., Microfluidic single-cell real-time PCR for comparative analysis of gene expression patterns., Nature Protocols, May 2012, 7(5):829-838.
Jokilaakso et al., Ultra-localized single cell electroporation using silicon nanowires., Lab on a Chip—Miniaturisation for Chemistry and Biology, Feb. 2013, 13(3):336-339.
Kim et al., Microfluidic sample preparation: Cell lysis and nucleic acid purification., Integrative Biology, 2009, 1(10):574-586.

(56) References Cited

OTHER PUBLICATIONS

Capoccia et al., How form follows functional genomics: gene expression profiling gastric epithelial cells with a particular discourse on the parietal cell., Physiological Genomics, Apr. 2009, 37(2):67-78.
Chen et al., Two-photon absorbing block copolymer as a nanocarrier for porphyrin: Energy transfer and singlet oxygen generation in micellar aqueous solution., Journal of the American Chemical Society, Jun. 2007, 129(33):7220-7221.
Diercks et al., Resolving Cell Population Heterogeneity: Real-Time PCR for Simultaneous Multiplexed Gene Detection in Multiple Single-Cell Samples., PLoS One, Jul. 2009, 4(7):e6326.
Oberwine et al., mRNA expression analysis of tissue sections and single cells., Journal of Neuroscience, Nov. 2001, 21(21):8310-8314.
Fan et al., Whole-genome molecular haplotyping of single cells., Nature Biotechnology, Jan. 2011, 29(1):51-57.
Gong et al., Massively parallel detection of gene expression in single cells using subnanolitre wells., Lab on a Chip, Sep. 2010, 10(18):2334-2337.
Greenfield et al., Application of environmental sample processor (ESP) methodology for quantifying Pseudo-nitzschia australis using ribosomal RNA-targeted probes in sandwich and fluorescent in situ hybridization formats., Limnology and Oceanography: Methods, Dec. 2006, 4(11):426-435.
Hatch et al., Tunable 3D droplet self-assembly for ultra-high-density digital micro-reactor arrays., Lap on a Chip—Miniaturisation for Chemistry and Biology, Aug. 2011, 11(15):2509-2517.
Hatch et al., 1-Million droplet array with wide-field fluorescence imaging for digital PCR., Lab on a Chip—Miniaturisation for Chemistry and Biology, Nov. 2011, 11(22):3838-3845.
Kalisky et al., Genomic Analysis at the Single-Cell Level., Annual Review of Genetics, Dec. 2011, 45:431-445.
Kamme et al., Single-Cell Microarray Analysis in Hippocampus CA1: Demonstration and Validation of Cellular Heterogeneity., Journal of Neuroscience, May 2003, 23(9):3607-3615.
Kazumori et al., Roles of caudal-related homeobox gene Cdx1 in oesophageal epithelial cells in Barrett's epithelium development., Gut, May 2009, 58(5):620-628.
Leedham et al., Individual crypt genetic heterogeneity and the origin of metaplastic glandular epithelium in human Barrett's oesophagus., Gut, Aug. 2008, 57(8):1041-1048.
Lewis et al., Regulation of heat shock protein message in Jurkat cells cultured under serum-starved and gravity-altered conditions, Journal of cellular biochemistry, Feb. 2000, 77(1):127-134.
Li et al., An improved one-tube RT-PCR protocol for analyzing single-cell gene expression in individual mammalian cells., Analytical and Bioanalytical Chemistry, Jul. 2010, 397(5):1853-1859.
Lidstrom et al., Life-on-a-chip., Nature Reviews Microbiology, Nov. 2003, 1(2):158-164.
Mary et al., Analysis of gene expression at the single-cell level using microdroplet-based microfluidic technology., Biomicrofluidics, Jun. 2011, 5(2):024109-024109-10.
Mueller et al., Profiling of microdissected gastric epithelial cells reveals a cell type-specific response to Helicobacter pylori infection., Gastroenterology, Nov. 2004, 127(5):1446-1462.
Scholin et al., The Environmental Sample Processor (ESP)—An Autonomous Robotic Device for Detecting Microorganisms Remotely using Molecular Probe Technology., Oceans 2006, 2006, p. 1-4.
Shi et al., Real-time PCR of single bacterial cells on an array of adhering droplets., Lab on a Chip—Miniaturisation for Chemistry and Biology, Jul. 2011, 11(13):2276-2281.
Soeller et al., Two-photon microscopy: Imaging in scattering samples and three-dimensionally resolved flash photolysis., Microscopy Research and Technique, Nov. 1999, 47(3):182-195.
Steinmeyer et al., Construction of a femtosecond laser microsurgery system., Nature Protocols, May 2010, 5(3):395-407.
Xia et al., Soft Lithography, Angewandte Chemie International Edition, Mar. 1998, 37(5):550-575.
Young, Optical applications of two-photon and microexplosion lithography., University of Washington, ProQuest Dissertations Publishing, 2007.
Zeng et al., Quantitative single-cell gene expression measurements of multiple genes in response to hypoxia treatment., Analytical and Bioanalytical Chemistry, Jul. 2011, 401(1):3-13.
Zeng et al., High-performance single cell genetic analysis using microfluidic emulsion generator arrays., Analytical Chemistry, Apr. 2010, 82(8):3183-3190.
Zhong et al., A microfluidic processor for gene expression profiling of single human embryonic stem cells., Lab on a Chip—Miniaturisation for Chemistry and Biology, 2007, 8(1):68-74.
Burgoyne, Optimal protocol for moulding PDMS with a PDMS master., Chips and Tips, Jul. 2010, retrieved Feb. 15, 2016. <http://blogs.rsc.org/chipsandtips/2010/07/06/optimal-protocol-for-moulding-pdms-with-a-pdms-master/>.
Qi et al., Probing single cells using flow in microfluidic devices., The European Physical Journal Special Topics, Apr. 2012, 204(1):85-101.
Olympus Corporation, A Full Line-up of Models to Meet Every Specific Purpose, from Microinjection to Patch Clamping., Micromanipulation System ON3 Series, Olympus ON3 Micromanipulator Catalogue, printed Mar. 2010.

\* cited by examiner

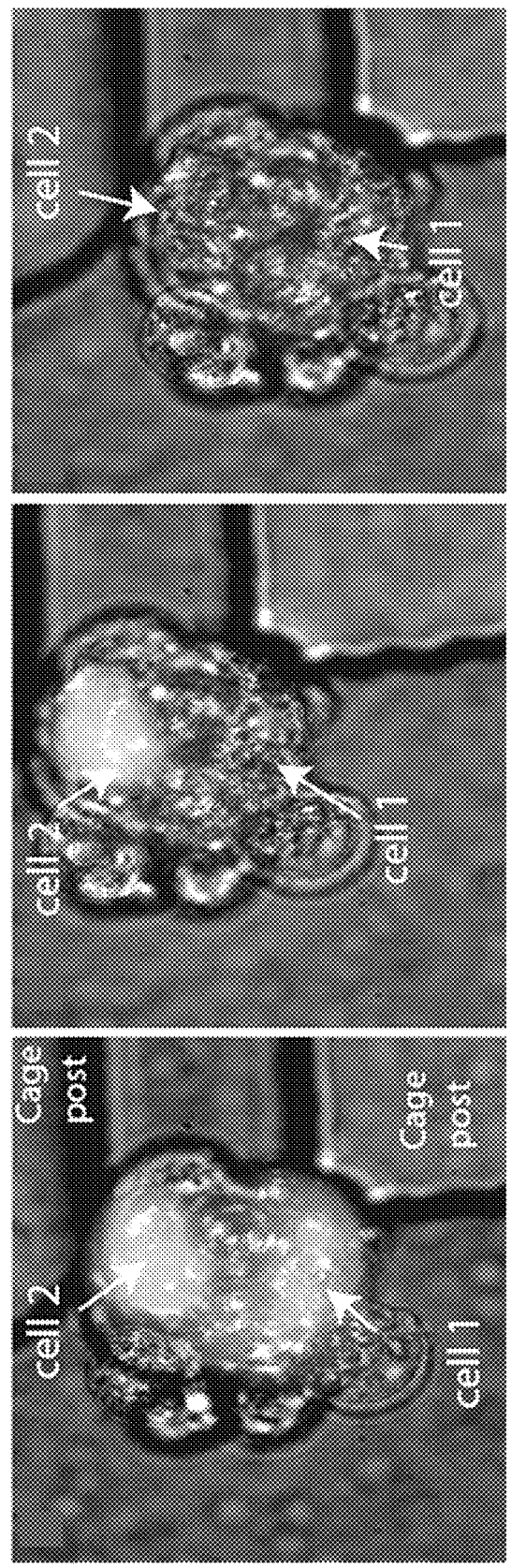

SYSTEM AND METHOD FOR LASER LYSIS

CROSS-REFERENCE TO RELATED APPLICATIONS

This application is a divisional application of U.S. national stage application Ser. No. 14/909,195 under 35 U.S.C. § 371 of PCT Application No. PCT/US2014/056960, filed Sep. 23, 2014, published as WO2015/048009, which claims priority under 35 U.S.C. § 119 from U.S. Provisional Application No. 61/883,739, filed Sep. 27, 2013, each of which is incorporated herein by reference in its entirety.

STATEMENT REGARDING FEDERALLY SPONSORED RESEARCH

This invention was made with government support under R21 CA174412 awarded by the National Institutes of Health. The government has certain rights in the invention.

BACKGROUND

The present disclosure relates to cellular analysis techniques, and more particularly, to systems and methods for in situ laser lysis for analysis of biological tissues (live, fixed, frozen or otherwise preserved) with single cell resolution.

Cells in living tissue have heterogeneous responses to environmental cues because of their differences in cell types, locations, exposure to blood supply, malignancy, and/or infection. For instance, cell-cell communication between cancer cells and their environments at the primary tumor and distant metastasis sites have been shown to be important for cancer development (Zhang W, et al. 2011, Cancer biology & therapy 11: 150-156; Calorini L, et al. 2010, Cell communication and signaling: CCS 8: 24). Recent technological advances in assessing gene expression at the single cell level have enabled advancements in the way in which investigators study diseases. The analysis of gene expression can be performed on live, preserved, and frozen tissues.

The introduction of commercially available microfluidic high-throughput systems further enables researchers to investigate problems at a larger scale (Citri A, et al. 2012, Nature Protocols 7: 118-127; Guo G, et al. 2010, Developmental Cell 18: 675-685). However, such methodologies may require cells to be dissociated from their native environments and therefore, may obscure valuable biological states that are influenced by multicellular complexity in situ. Current tools are not able to capture lysate from individual cells in situ, especially making it difficult to analyze the individual live cells given the short-lived nature of RNA, which can degrade on time scales of seconds to minutes, as well as the fast response time of the cellular gene-expression machinery on the order of minutes.

One single-cell lysate harvesting approach includes a vacuum-like mechanical probe to continuously release lysis buffer through a microchannel and draw in liquid surrounding target cells (Sarkar A, et al. 2014, Nature Communications 5). However, the size of the probe head resulted in a physical limitation with respect to accessing the target cells. Moreover, the time required for cell lysis is relatively lengthy at around 1 minute. Finally, harvesting a quantity of cells to acquire statistically significant results can be in excess of one hour, which may trigger cellular stress responses to the surrounding cells. Accordingly, it would be useful to provide a system and method for single cell analysis which can be accomplished under biologically relevant conditions and on biologically relevant time-scales.

SUMMARY OF THE DISCLOSURE

The present invention overcomes the aforementioned drawbacks by providing a system and method for in situ laser lysis for analysis of tissue (including but not limited to live, preserved, or frozen) at the single cell resolution.

In accordance with one aspect of the present disclosure, a method for lysing individual cells in situ includes the steps of capturing a tissue sample comprising a cellular content, subjecting the tissue sample to a stream of continuous fluid flow, lysing a selected area of the tissue sample with a laser, thereby releasing at least a portion of the cellular content from the tissue sample, recovering at least one target molecule from the cellular content in the stream, and processing at least one target molecule.

In accordance with another aspect of the present disclosure, a system for lysing cells, includes a microfluidic chip having a fluid channel and a cage disposed within the fluid channel, the cage sized to capture a tissue sample, a microscope for observing the tissue sample, a laser for irradiating a selected area of the tissue sample, and a downstream module coupled to the microfluidic chip for processing a target molecule collected from the tissue sample. Irradiating the tissue sample with the laser lyses the selected area of the tissue sample, thereby releasing the target molecule from the tissue sample into the fluid channel.

In accordance with a further aspect of the present disclosure, a device includes an apparatus including a body defining a passage, a capillary in fluid communication with an inlet of the passage, and an output port in fluid communication with an outlet of the passage. The device further includes a removable microfluidic chip coupled to the body, the microfluidic chip including a first fluid channel having an inlet and an outlet in communication with the passage, and a cage positioned between the inlet and the outlet, the cage comprising a plurality of structures sized to retain a tissue sample in the first fluid channel.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

An ultrafast (pulsed) laser lyses a cell of interest in a tissue (including but not limited to live, preserved, or frozen) via a two-photon (2P) process. The system collects cellular contents, performs highly multiplexed RT-qPCR or RNA-seq, and sequentially (cell-by-cell) reconstructs a 3D spatial map of mRNA expression with a large number of genes. A 3D spatial map of the DNA, RNA, and/or proteins can be generated for each cell in the tissue.

Figure 9:
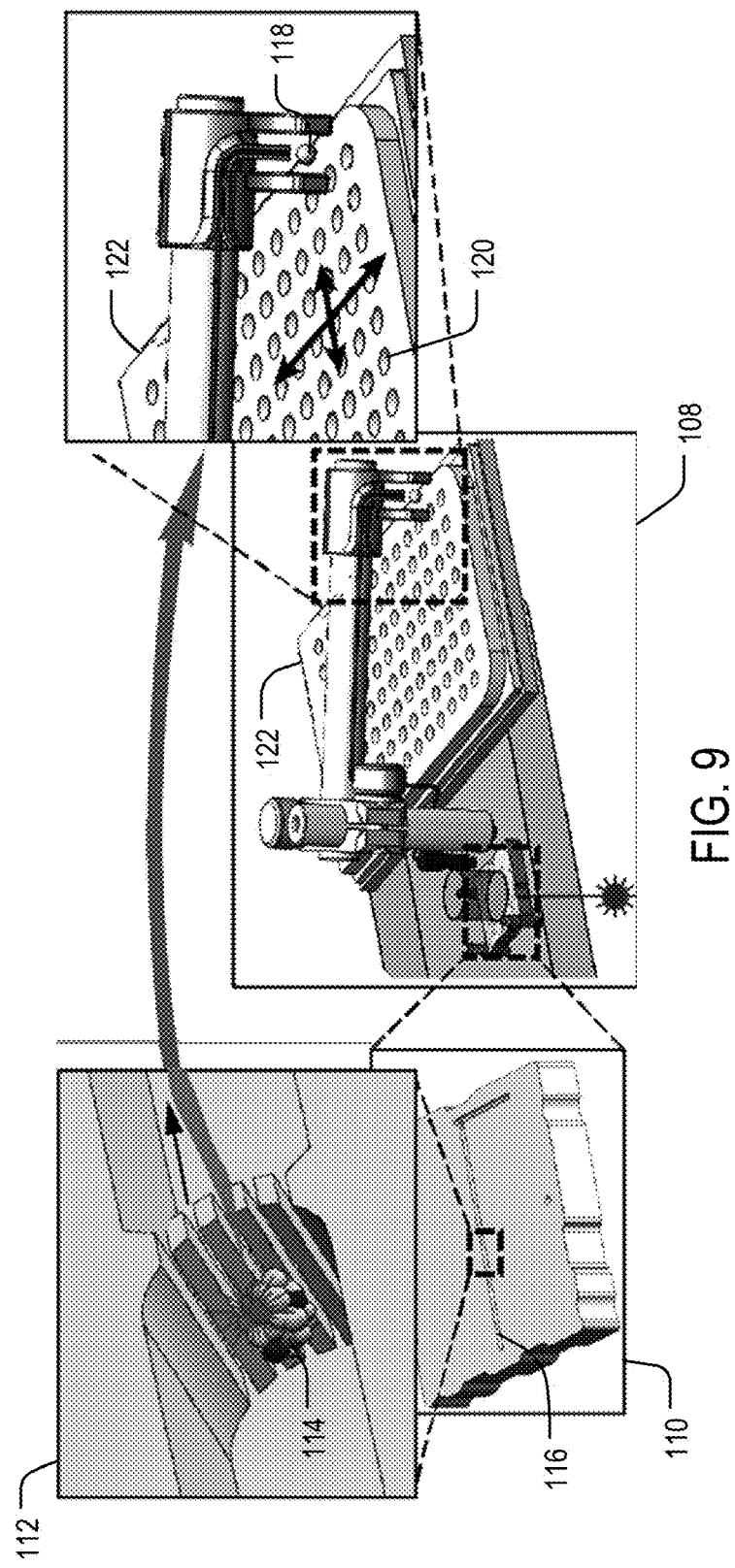

FIG. 9 is a schematic illustration of a microfabricated cage in a microfluidic cassette for holding a tissue sample during lysis. The 'plume' of cellular contents may be collected downstream of the channel, and the microfluidic cassette may be implemented on a fluorescence microscope with a motorized X-Y-Z stage. A tube connects the outlet of the microfluidic cassette with, and dispenses the cell lysate into a well of a 96-well plate. Dispensing may be controlled by a drop sensor at the tubing end. After lysis, a plurality of analyses, such as reverse transcription and pre-amplification of the collected RNA samples may be performed.

Figure 10:
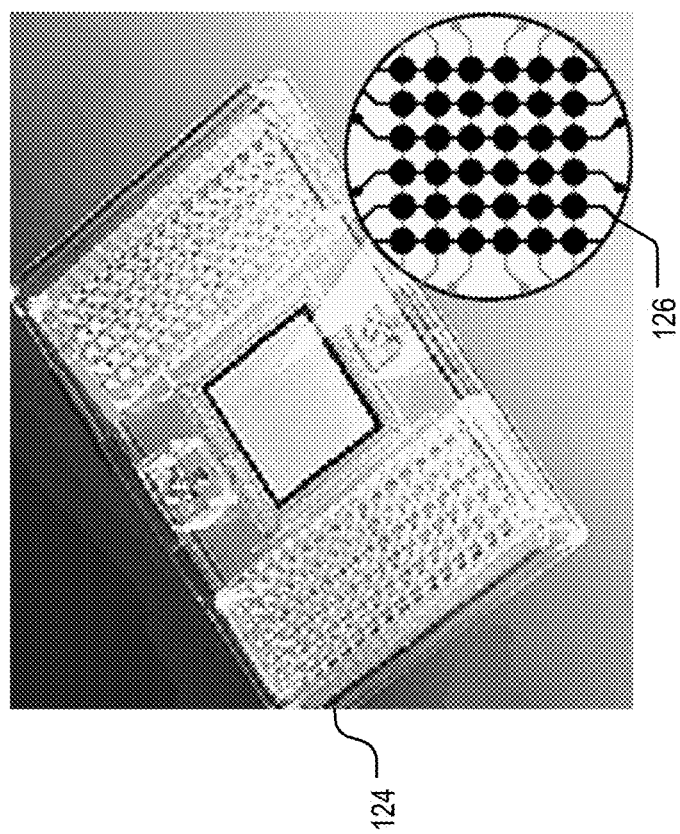

FIG. 10 is a photographic image of an example device for performing qPCR with an integrated analysis platform. The device includes an integrated fluidics circuit which has 96×96 PCR micro-chambers capable of analyzing 96 genes in each of the 96 single-cell samples.

Figure 11C:
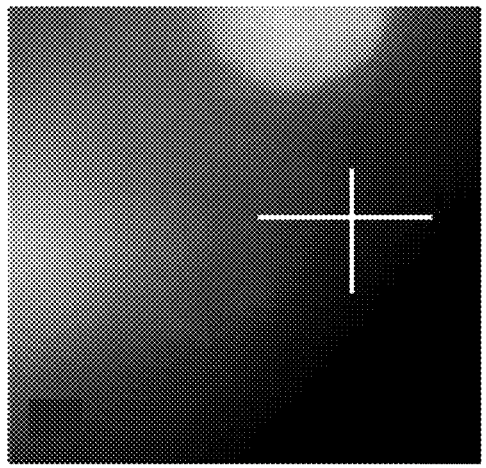
Figure 11B:
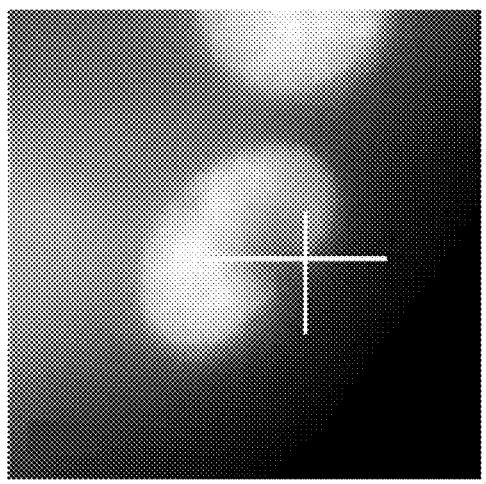
Figure 11A:
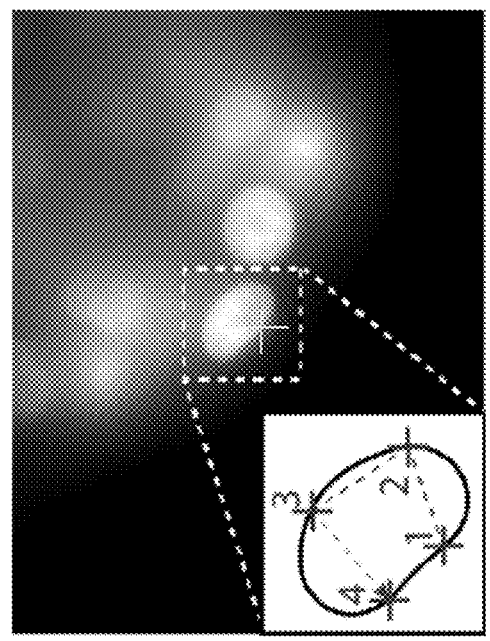

FIG. 11A is a fluorescence image of a stained nuclei recorded during lysis. The crosshair at the center indicates the position of the focused 2P laser beam. The insert shows the four lysis locations and the sequential lysis pattern on one of the nuclei.

FIG. 11B is an enlarged partial view of FIG. 11A. Irradiation with a 100 ms long pulse train resulted in significant rupture of the nucleus.

FIG. 11C is a fluorescence image illustrating the nucleus after irradiation with four pulse trains targeted at locations shown in FIG. 11A.

FIGS. 12A-12C are combined fluorescence and brightfield micrographs showing two-photon laser lysis (2PLL) of individual cells in an intact live 3D cell cluster. FIG. 12A is an image of the cell cluster immobilized in the microfabricated cage. FIGS. 12B and 12C show sequential application of the 2PLL to two green fluorescent protein (GFP) positive cells demonstrating accurate lysis events that are highly confined to the separate target cells with no effect on adjacent cells.

Figure 13:
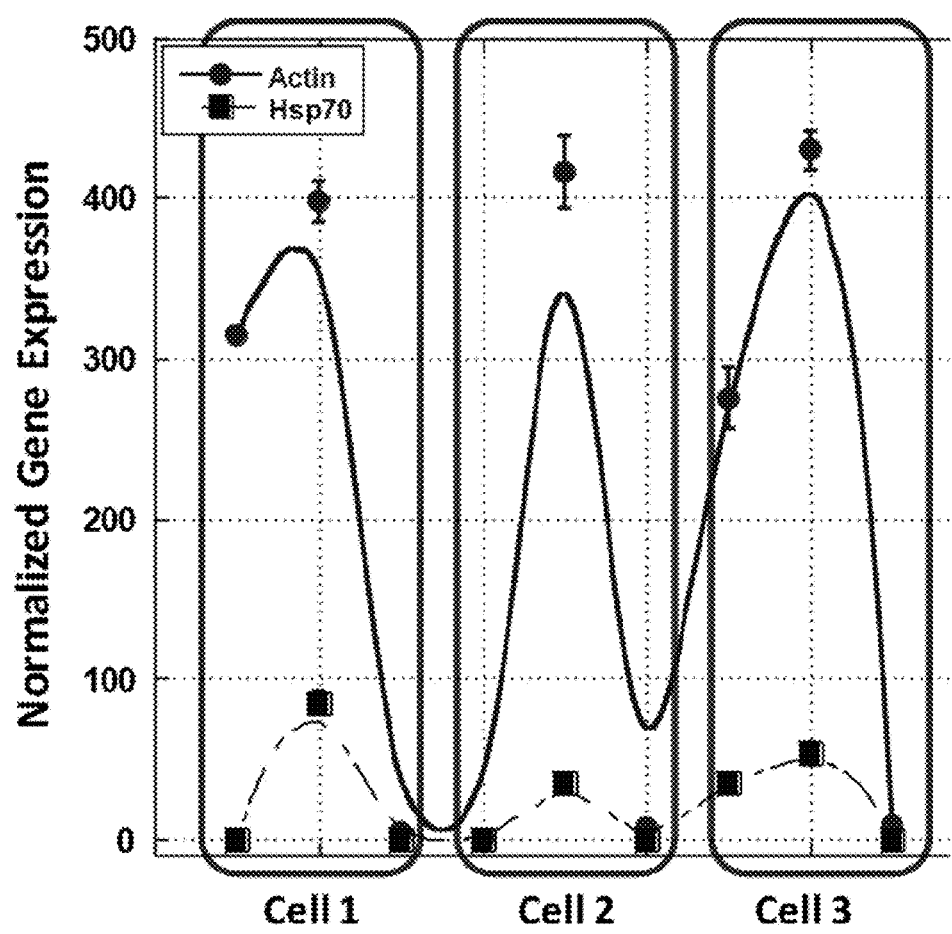

FIG. 13 is a plot demonstrating the ability of SQUIRT-PCR to lyse and collect single cell contents with minimal carryover contamination from two sequential lysis events and negligible cellular stress. The data was obtained with three individual cells where each cell was lysed and cell contents were collected in three sequential 60 µl fractions. The solid curve is a best-fit line to the β-actin mRNA levels across the fractions from all three cells. The β-actin level was the highest in the first two fractions and subsequently returned to the background level after the 3rd collection. This finding clearly suggests that SQUIRT-PCR efficiently collects RNA samples from single cells and the fluid flow conditions effectively eliminate carryover contamination between cell lysing events. The dashed curve represents a fit to the HSP70 mRNA which was at low levels in the three cells. Notably, the initial lysing event of the first cell did not induce HSP70 gene expression in the second two cells, which indicates that laser lysis does not induce cellular stress during cell lysis.

Figure 14:
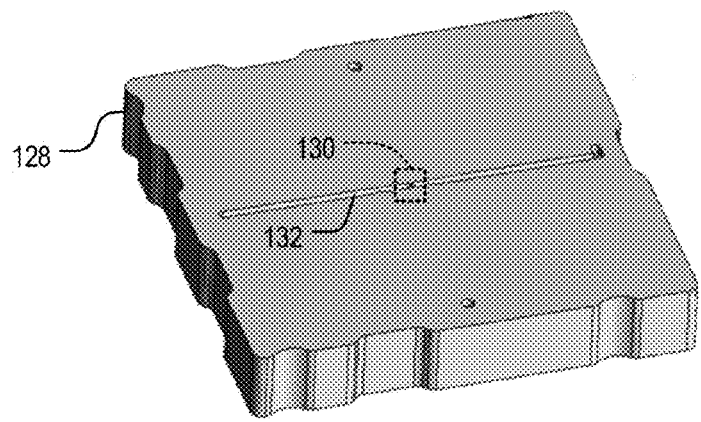
Figures 15A, 15B, 15C, 15D:
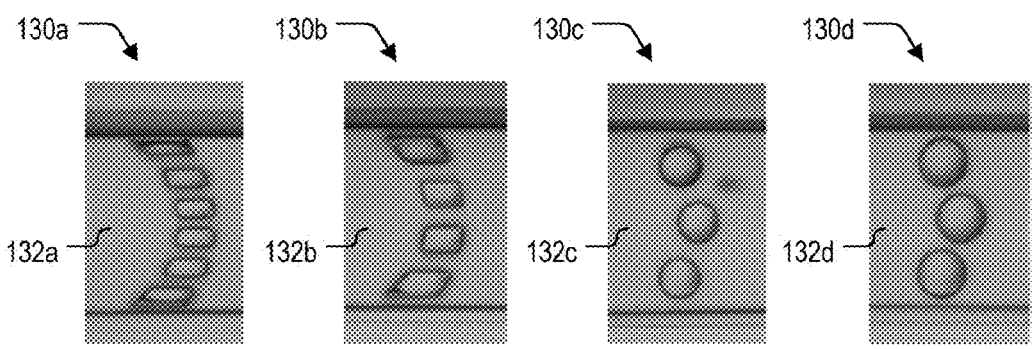

FIG. 14 is a schematic illustration of an example microfluidic chip with a tissue capture cage according to the present disclosure.

FIGS. 15A-15D are optical images showing four different embodiments of the microfabricated cage for immobilization of tissue clusters.

Figure 16:
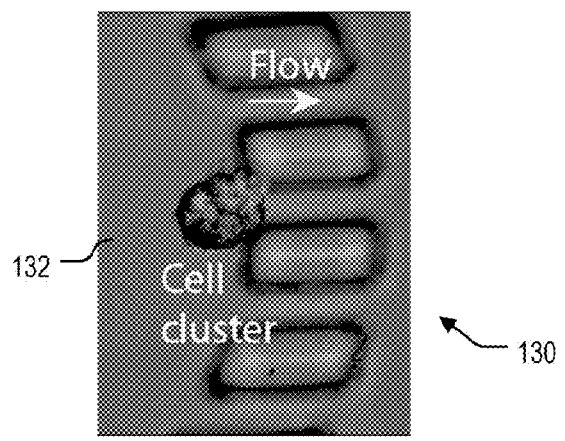

FIG. 16 is an optical image of a cell cluster trapped in an example cage according to FIG. 14.

Figure 17C:
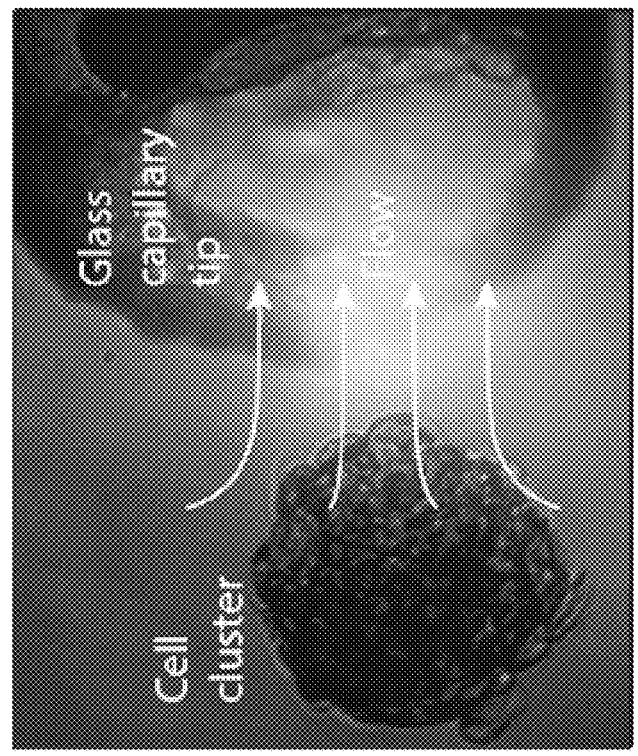
Figure 17B:
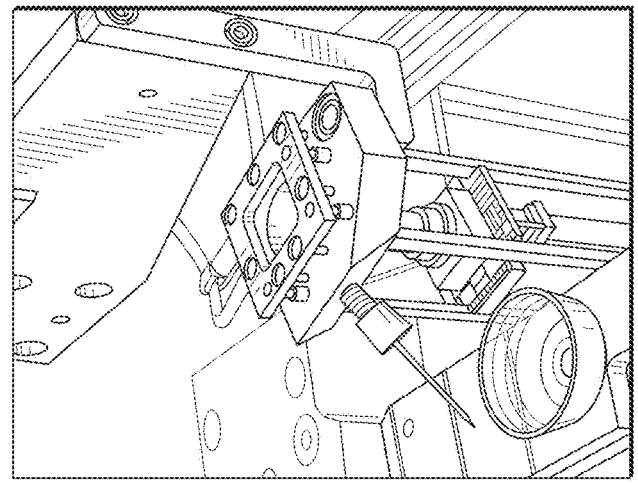
Figure 17A:
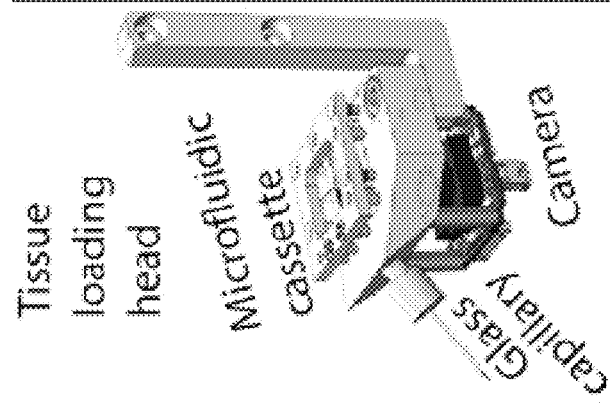

FIG. 17A is a 3D model of an example platform for loading a single tissue sample into the microfluidic cassette. The model includes the loading head including a glass capillary, the microfluidic cassette on its top, and a miniature camera on the bottom.

FIG. 17B is a picture showing a possible embodiment of the loading head in FIG. 17A mounted on a motorized microscope stage.

FIG. 17C is a micrograph of a target cell cluster with the tip of a glass capillary on the right.

Figure 18C:
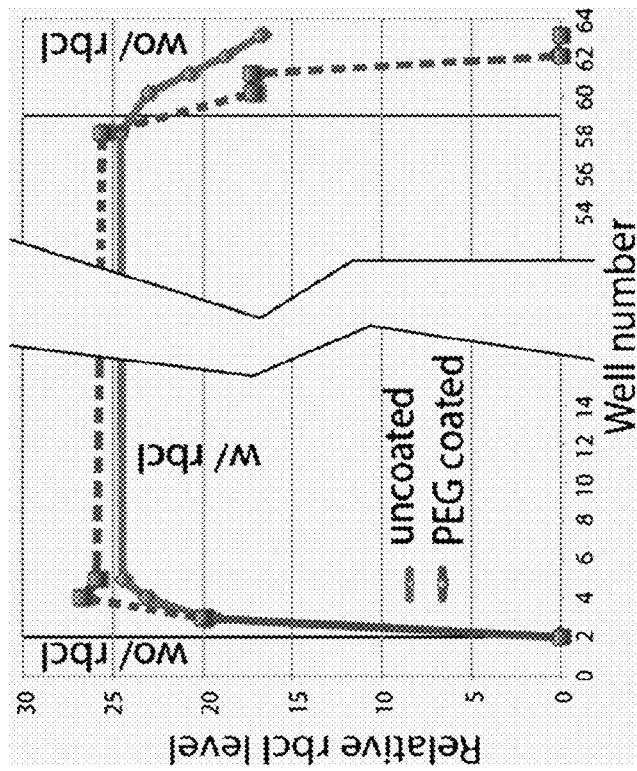
Figure 18A:
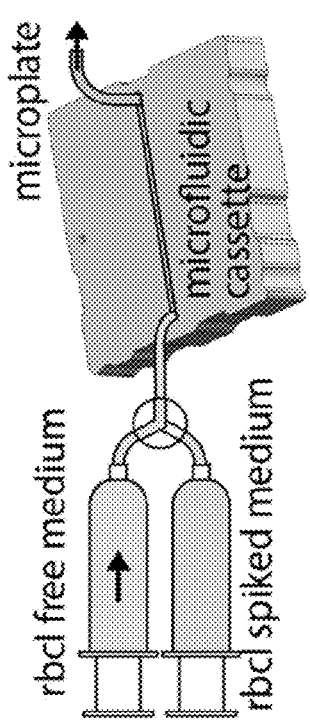
Figure 18B:
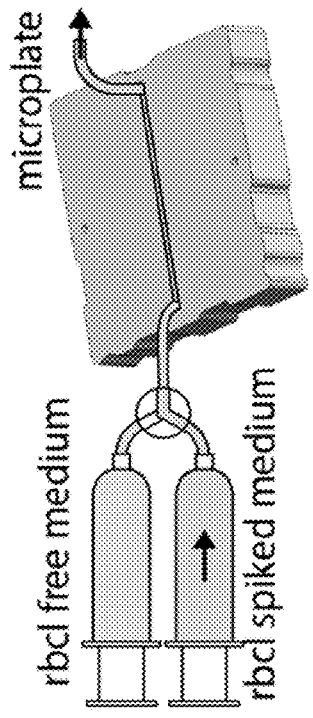

FIGS. 18A and 18B are schematic illustrations of an experimental design for evaluating a PEG-treated PDMS chip which included one syringe filled with cell medium and another syringe filled with cell medium+RBCL mRNA that passed through a valve, the microfluidic chip, before being deposited into a 96-well plate. After flushing the entire system with water, the system was primed with a solution of medium and RNA up until the valve. The valve was then switched to allow only RNA-free medium to flood the entire system up until reaching the microtiter plate. At this point, the valve was switched to allow the RBCL RNA-rich medium to flow through the chip before the collection started into the 96-well plate.

FIG. 18C is a plot of RT-qPCR analysis showing RBCL levels in the flow-through samples collected from untreated (solid line) and PEG-treated (dashed line) samples as a function of collected volume represented in well numbers. Data was collected with the experimental setup shown in FIGS. 18A and 18B. The volume collected per well as about 40 (about 3 drops).

Like numbers will be used to describe like parts from Figure to Figure throughout the following detailed description.

DETAILED DESCRIPTION OF THE INVENTION

The present invention is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention.

In general, one aspect of the present disclosure includes a system and method for laser lysis of individual cells in situ without the requirement of disaggregating tissues a priori. The proposed laser lysis method may be used in any setting for any kind of single-cell analysis that requires harvesting of single cell contents and, in addition to DNA and RNA, may be utilized for collecting proteins or other biological molecules of interest. The in situ laser lysis device may be used in connection with any downstream module capable of collecting single cell contents. In one aspect, cells in live tissue may respond to environmental insults differently because of their inherent differences in cell types, locations, exposure to blood supply, intrinsic heterogeneity, infection, or a combination thereof. Hence, the disclosed in situ laser lysis system may provide single cell contents from tissue at known locations. The system and method may allow for the comprehensive analysis at the genomic, transcriptional, and protein expression levels in healthy tissues, diseased cells (e.g., cancer), their neighboring cells in a diseased (e.g., cancer) tissue, and the like. Accordingly, the present disclosure may provide a better understanding of how cell-cell communication takes place in diseased tissue in situ.

In one embodiment of the present invention, the in situ laser lysis device may allow a user to perform single cell in situ quantitative reverse transcription polymerase chain reaction (SQUIRT-PCR) for in situ gene expression heterogeneity analysis using mRNA collected from individual cells. The device may include a two-photon laser in order to separately lyse a sequence of individual cells, one cell at a time, located at known coordinates within a three-dimensional (3D) tissue or cell cluster. Further, this system may allow for rapid release of cellular contents from different individual cells for a plurality of downstream analyses, including quantitative reverse transcription polymerase chain reaction (RT-qPCR) profiling. In one aspect, cellular contents may include DNA (chromosomal, plasmid, and the like), RNA (mRNA, non-coding RNA, ribosomal RNA, and the like), protein, small molecules, membrane components, and the like. In one embodiment, the single-cell lysate may be immediately transported to an emulsion-based (oil-droplet) RT-qPCR module to profile mRNA expression. Accordingly, the present disclosure may provide for a highly multiplexed platform capable of detecting dozens of mRNA sequences from each droplet of the single cell lysate.

In one aspect, any suitable method for the lysis of cell or tissue samples may be employed. For example, the cells to be analyzed may be individually held on a substrate, conglomerated into a tissue (or cell cluster) sample, or the like. Embodiments of a system may allow for indefinite sampling at the single cell level. In one aspect, sampling may be carried out to better understand the distribution of DNA markers or RNA markers in larger collections of cells or tissues. In another aspect, information of the spatial location of each cell in the tissue may be retained, thereby enabling a better understanding of cellular heterogeneity and the functional relevance in tissues.

In some embodiments, a system and method for in situ single cell laser-lysis may include a microfluidic chip. In one example, a tissue sample may be selected and then loaded into the microfluidic chip. In some embodiments, the tissue sample may have a dimension of about 100 µm to about 300 µm. In other embodiments, the sample may include one or more individual cells, multiple cells or tissues. The sample may be acquired from any suitable source, such as from a batch of similar tissue samples (or individual cells) floating in media.

In some embodiments, sample collection may be performed with a Tissue Collection Device (TCD), which may be coupled to a microfluidic chip according to the present disclosure. A TCD may allow for the capture of a tissue sample (or individual cell) and placement of the sample into a cage or other containment device included in the design of the microfluidic chip.

Figure 1:
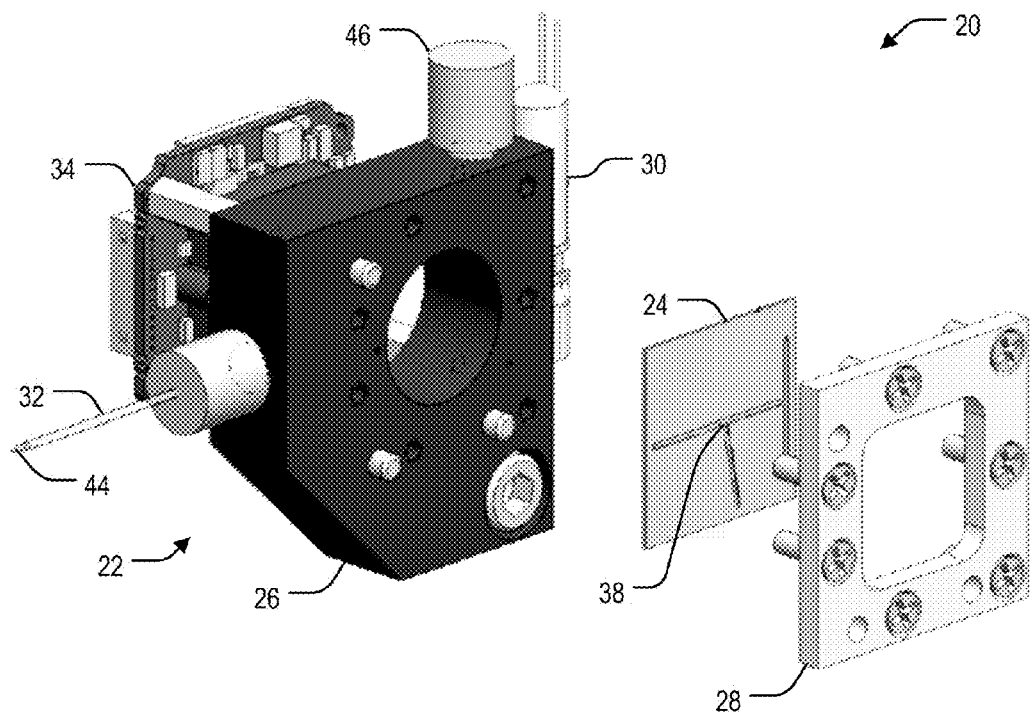
FIG. 1 is an illustration of one example of a tissue collection device and microfluidic chip according to the present disclosure.

Turning now to FIG. 1, and embodiment of a TCD 20 may include an apparatus 22 and a microfluidic chip 24. The apparatus 22 may have a body 26, a clamp plate 28, a control valve 30, a capillary 32, a camera 34 and an output port 36. The microfluidic chip 24 may be a two part assembly including a microfabricated polydimethylsiloxane (PDMS) component and a glass slide. The microfluidic chip 24 may be manufactured by microfabricating a master mold out of a silicon wafer, then pouring degassed PDMS liquid over the mold, and after curing, removing PDMS.

Figure 2:
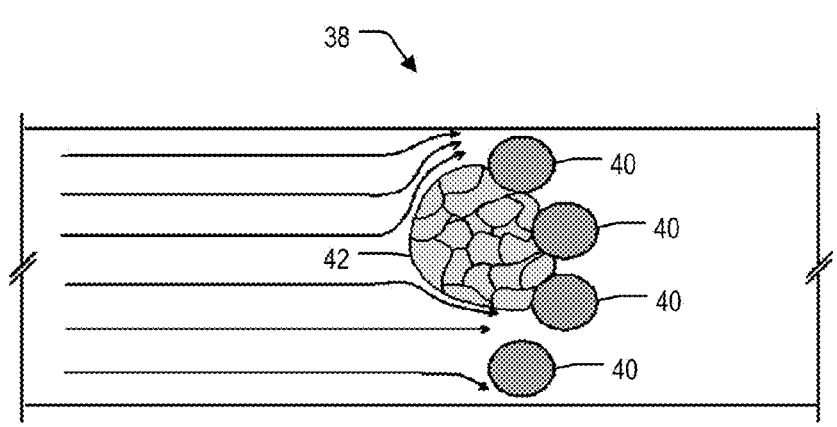
FIG. 2 is a schematic illustration of a tissue capture cage within a microfluidic channel of the microfluidic chip of FIG. 1.

With reference to FIGS. 1 and 2, the microfluidic chip 24 may include a cage 38. The cage 38 may include a plurality of posts 40 or other like baffles to prevent the passage of a cell or tissue sample 42 flowing therethrough. Accordingly, the cage 38 may have a specific size and geometry to allow the capture of the tissue sample 42 while still allowing a fluid flowing through the cage 38 to wash away the lysed cell contents. Note that arrows shown in FIG. 2 are indicative of the direction of fluid flow. Also, it will be appreciated that a system and method may be compatible with both tissue samples and single cell samples.

One aspect of the present system and method may include the ability to select and collect a particular tissue sample from a multitude of free floating tissue samples and deliver said sample to a confined space within a microfluidic channel. Another aspect of the present system and method may include the ability to transfer a captured tissue sample to a downstream device. Examples of downstream devices may include analytical devices, instrumentation or characterization platforms for performing tissue-level analysis.

In some embodiments, an array of tissue samples may be maintained in a media bath. The capillary 32 of the TCD 20 may be lowered into the bath, such as with an automated system with visual feedback. Once a tip 44 of the capillary 32 is in proximity to the tissue sample 42 in the media bath, the tissue sample 42 may be drawn into the capillary 32, such as with a source of vacuum in communication with an output line 46 of the TCD 20. As the tissue sample 42 flows through the TCD 20 and into the microfluidic chip 24, the tissue sample 42 may eventually become caught in the cage 38 of the microfluidic chip 24 as shown in FIG. 2. At this point, a user may observe the tissue sample 42 with the camera 34. Thereafter, the user may turn off the control valve 30, thereby locking the TCD 20 into a steady-state in which the microfluidic chip 24 may be removed from the TCD 20. In some embodiments, the tissue sample 24 retained on the microfluidic chip 24 may be incubated for a period of time by transferring the microfluidic chip 24 from the TCD 20 to an incubator for facilitating surface bonding.

In other embodiments, the microfluidic chip 24 may be transferred to a microscope plate for analysis with a microscope inspection station.

Figure 3A:
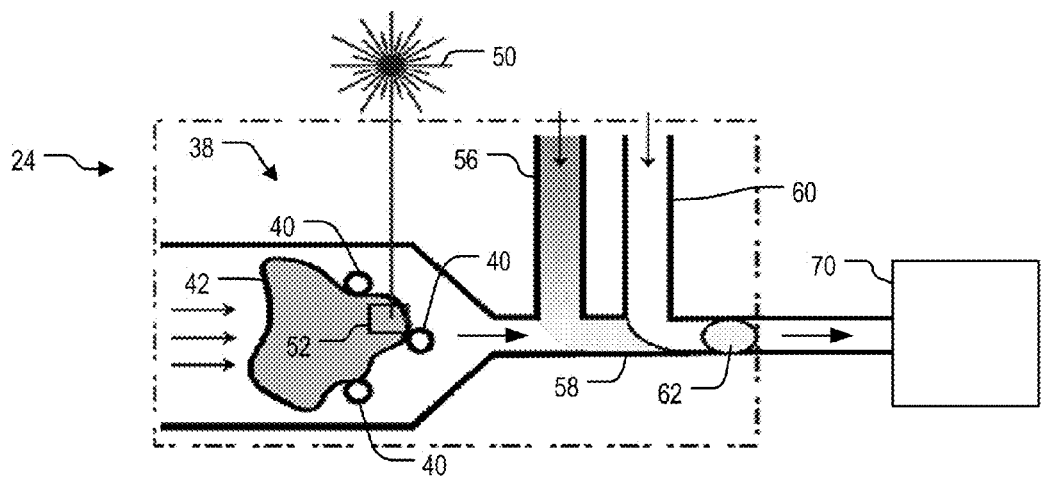
FIG. 3A is a schematic illustration of a laser lysis process performed on a captured tissue sample. The tissue sample may be irradiated with a two-photon laser and the lysate collected and combined with one or more components prior to encapsulation.
Figure 3B:
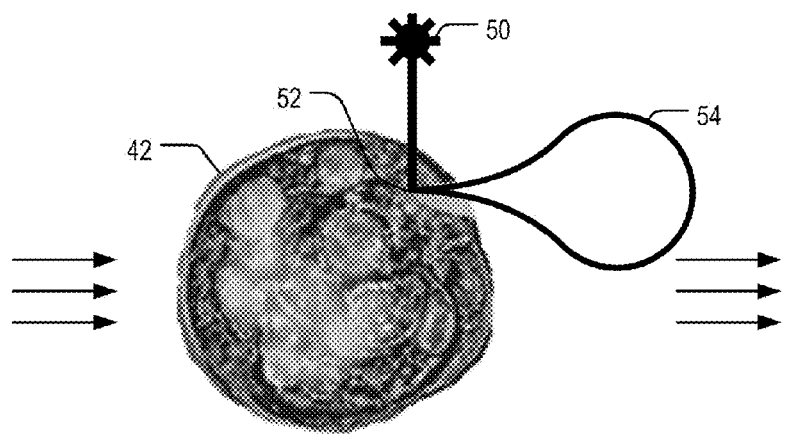
FIG. 3B is an enlarged view of an actual tissue sample schematically shown in FIG. 3A.

With reference to FIGS. 3A and 3B, the cell or tissue sample 42 on the microfluidic chip 24 may be subjected to a sheath of continuous fluid (e.g., buffer) flow as indicated by the arrows. In some embodiments, the microscope plate containing the microfluidic chip 24 may be set up on a microscope station equipped with a laser 50. The microscope may visualize the tissue sample 24. The user may select a target area 52 of the tissue sample 24 to be lysed. Using the laser 50, the selected target area 52 of the tissue sample 24 may be irradiated with the laser 50, thereby releasing at least a portion of the contents 54 of the target area 52 of the tissue sample 24. The contents 54 may then flow downstream in the fluid flowing through the microfluidic chip 24. In one aspect, spatial data (e.g., positional coordinates) for each cell in the tissue sample 42 may be collected and stored while allowing for continuous lysis of the individual cells within the tissue sample 42 as shown in FIGS. 3A and 3B.

Figures 4A, 4B:
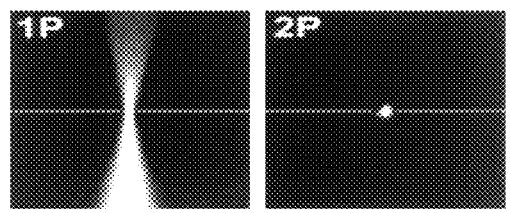
FIG. 4A is an illustration of single-photon (1P) laser excitation intensity profile.
FIG. 4B is an illustration of two-photon (2P) laser excitation intensity profile.

In some embodiments, the laser 50 may be a two-photon laser. With reference to FIGS. 4A and 4B, the laser profiles for a single photon (1P) laser may differ from that of a two-photon (2P) laser. Nonlinear two-photon excitation concentrates energy in a femtoliter-scale volume, and may therefore allow precise subcellular operations (Heisterkamp A, et al. 2005, Optics Express 13: 3690). The excitation may be rapid, highly localized, and the process may be compatible with optical microscopes. Two-photon laser lysis is different from the conventional single-photon-based lysis methods that have poor axial resolution for 3D structures (Dhawan M, et al. 2002, Analytical and Bioanalytical Chemistry 374: 421-426; Lai H-H, et al. 2008, Journal of The Royal Society Interface 5: S113-S121; Quinto-Su P A, et al. 2008, Lab Chip 8: 408-414; Rau K R, et al. 2006, Biophysical Journal 91: 317-329; Rau K R, et al. 2004, Applied Physics Letters 84: 2940-2942; Sims C E, et al. 1998, Anal Chem 70: 4570-4577). In one aspect, the present system and method may combine two-photon excitation to lyse cells in tissues and sequentially harvest their cell contents automatically.

Tuning again to FIGS. 3A and 3B, a RT-qPCR module 70 may be in downstream communication with the microfluidic chip 24. In this case, the lysed single-cell contents 54 (e.g., DNA, RNA, protein, small molecules and the like) may mix downstream with a stream 56 including, for example, components for performing RT-PCR (e.g., primers and RT-PCR master-mix) in a stream 58 on the microfluidic chip 24. Primers and other components present in stream 56 may be provided to facilitate the amplification of nucleic acid templates (e.g., DNA, RNA) in the downstream qRT-PCR module 70. Further downstream in the microfluidic chip 24, the stream 58 may mix with an oil containing stream 60. Accordingly, the contents of stream 58 may be distributed into discrete droplets 62 by the perpendicular flow of oil from stream 60.

In one aspect, the aqueous stream 58 may not mix with the oil stream 60. In another aspect, the volume of droplets 62 may be controlled by varying the flow rate of the stream 58 and the stream 60, the geometry of the microfluidic chip, or the like. The aqueous phase contents of droplets 62 may continue to mix as the droplets 62 flow downstream. In one aspect, the microfluidic chip 24 may be configured to enable the contents of the droplets 62 to achieve homogeneity by the time the droplets 62 reach the RT-qPCR module 70.

Figure 5:
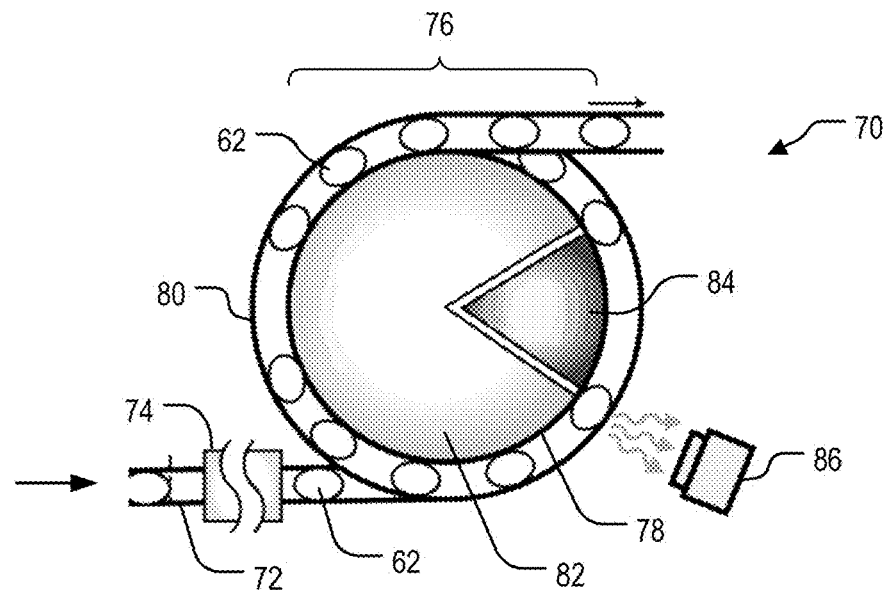
FIG. 5 is a schematic illustration of an RT-qPCR module.

Turning now to FIG. 5, the droplets 62 may flow from the microfluidic chip 24 into a small diameter passage 72 of the downstream RT-qPCR module 70. The passage 72 may be continuous and may extend the length of the entire qRT-PCR module 70. The droplets 62 may come into contact with a first sub-system 74 for performing reverse transcription (RT). In one aspect, the sub-system 74 may be uniformly heated to convert RNA in the droplets 62 to cDNA. One suitable temperature for heating the sub-system 74 to may be about 40 degrees Celsius. The droplets 62 may continue to flow downstream through the subsystem 74 to a subsystem 76 for performing PCR. The subsystem 76 may include a dual-zone heating block 78. Fluid tubing 80 may wrap around the periphery of the heating block 78 one or more times. For example, the number of time the fluid tubing 80 wraps around the heating block 78 may equal the number of amplification cycles the experiment calls for (e.g., 40 cycles=40 wraps). A first zone 82 of the heating block 78 may be maintained at a temperature (e.g., about 95° C.) to carry out a denaturing step of a PCR protocol. A second zone 84 of the heating block 78 may be maintained at a temperature (e.g., about 60° C.) to carry out an annealing/extension step of a PCR protocol.

The subsystem 76 may further include a fluorescence detector 86. The fluorescence detector 86 may be used to monitor each amplification cycle of a PCR protocol. The fluorescence signal may be obtained by exciting the droplets 62 with an LED, laser source or other suitable excitation source. The fluorescence detector 86 may measure the fluorescence emission from the droplets 62 with any suitable detector, such as a photodetector, photomultiplier tube, charge coupled device or the like. The data from the fluorescence detector 86 may be read and processed by software. After the subsystem 76 the tubing 80 and thus droplets 62 may flow to a downstream container (not shown).

In some embodiments, fluids (buffer, primers, master-mix, oil) flowing through the microfluidic chip 24 or RT-qPCR module 70 may be controlled by a pressure-driven pumping system that allows for a smooth, continuous flow. The hardware components, control systems, data collection and processing may be carried out with software. Data collected from the TCD 20 or RT-PCR module 70 may be output in real-time to a monitoring system. Accordingly, a user may store the data for later use, or adjust system parameters based on the design of the experiment.

In some embodiments, it may be possible to apply different perturbagens upstream of the tissue sample 42 so as to discover their effects with real time exposure. If extended exposure is necessary, the perturbagen may be introduced into the microfluidic chip 24 and all flow stopped while the effect was put to the tissue sample 42. The perturbagen may then be washed away, and, optionally, a second perturbagen may be introduced. This may be used to discover the effects of multiple dosing on patients organ cells.

Figure 6A:
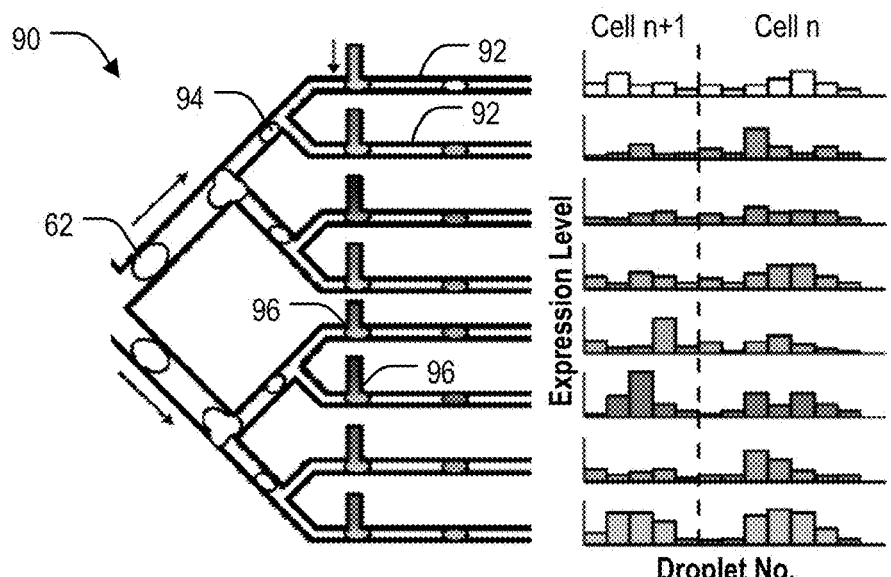
FIG. 6A is a schematic illustration of a multi-channel microfluidic device for the preparation of sample lysates with different compositions of reagents (e.g., PCR reagents) for downstream analysis, and the corresponding expression level profiles for each prepared droplet.
Figure 6B:
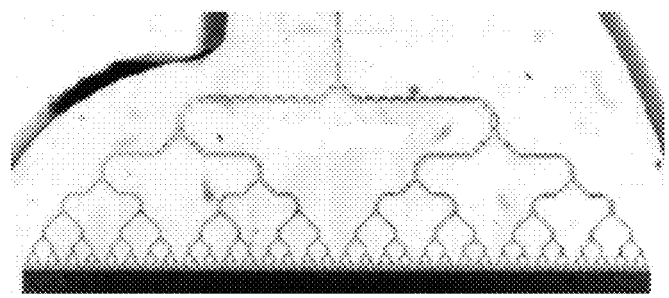
FIG. 6B is a bright field image of an example microfluidic device according to FIG. 6A.

In some embodiments, DNA, RNA or other cellular components inside the microfluidic chip 24 may be partitioned or encapsulated into much smaller droplets separated by oil and directed into different channels of a multi-channel splitter 90 as shown in FIGS. 6A and 6B. Each channel 92 may be individually addressed with a different composition (e.g., primers, master-mix and the like) that may be combined with the microdroplet 94 during passage through the combination junction 96. The microdroplets 94 may be combined into a single stream of separated microdroplets in communication with a downstream RT-qPCR module, maintained in multiple distinct passages that may be wound through the RT-qPCR module, or a combination thereof. For example, the number of tubes wrapped around the PCR module may equal forty times the number of separated microchannels 92.

In some embodiments, the microfluidic chip 24 may be maintained to provide a suitable microenvironment for the tissue sample 42. In one aspect, the microfluidic chip 24 may be transparent for compatibility with one or more optical microscopes, lasers or other analytical equipment. Moreover, the structure of the microfluidic chip 24 may be configured to reduce physical stress that may be imparted to the tissue sample 42, for example, to minimize artificial bias.

Figure 7:
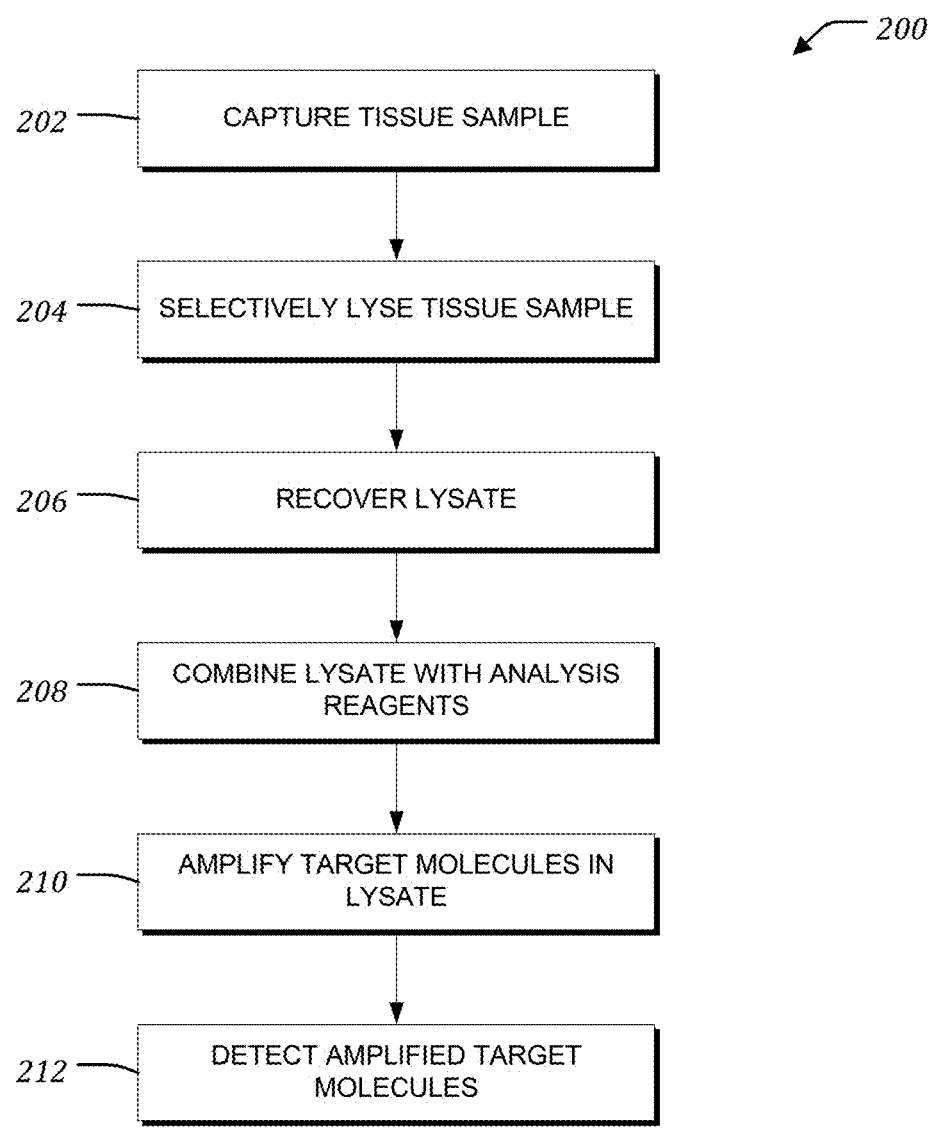
FIG. 7 is a workflow example of a method for performing SQUIRT-PCR according to the present disclosure.

Turning to FIG. 7, an example method 200 for performing SQUIRT-PCR may include a first step 202 in which a tissue sample is captured. As described herein, a tissue sample may include a single cell or a portion thereof as well as a plurality of cells or tissues. The tissue sample may be captured using any suitable device such as a TCD or other device configured to capture, retain or otherwise isolate a tissue sample. Thereafter, in a step 204, the tissue sample may be selectively lysed. Lysis may include the use of a laser (e.g., a two-photon laser) to target one or more portions of a tissue sample. Lysis may further include the use of a microscope to visualize the tissue sample. Visualization may be useful for guiding the laser or other lysing apparatus in order to target a particular area or portion of the tissue sample for lysis.

Following lysis, a step 206 may include recovery of the lysate. In one aspect, it may be useful to retain the tissue sample or portions thereof while recovering soluble portions of the lysate. For example, it may be useful to recover DNA, RNA, small molecules, proteins, or the like. The method of recovering the lysate may include a microfluidic device for capturing the selected portions of the tissue while enabling other portions to be partitioned for recovery. A step 208 may include combing the recovered lysate from the step 206 with analysis reagents. Suitable analysis reagents may include, primers, buffer, salts, polymerase, dyes, solvents (e.g., betain, DMSO), reverse transcriptase, nucleotides and the like. For example, it may be useful to combine the lysate with reagent for performing RT-qPCR. The step 208 may further include encapsulating the combined lysate and reagents. For example, the aqueous lysate and reagents may be combined with an immiscible organic material such as oil.

In a step 210, the combined lysate and reagents may be subjected to one or more amplification processes. Example amplification processes may include thermal cycling processes or protocols for performing reverse transcription, preamplification, polymerase chain reaction and the like. In one aspect, DNA or RNA templates present in the lysate may be amplified for detection in a step 212, wherein target molecules present in the lysate may be detected. Target molecules may include DNA, RNA, small molecules, proteins and the like. In one example, optical detection method may be used to qualitatively or quantitatively analyze the amplified target molecules.

It will be appreciated that in some embodiments, one or more steps of the method 200 may be omitted. For example, in the case that a target molecule includes a protein that may be present in the recovered lysate, it may be useful to omit an amplification step. Instead (or in addition), it may be useful to recover the protein target molecule for analysis with another technique such as mass spectrometry or nuclear magnetic resonance. Other variations of the method 200 may also fall within the scope of the present disclosure.

In general, the in situ single cell laser lysis system of the present invention may enable more accurate gene expression profiling of cells as the single-cell contents may flow directly from the tissue to RT-qPCR in a relatively short time as compared with other systems. In one aspect, the small scale of the microfluidic channels within the in situ laser lysis device may enable the use of microliter scale volumes for sample processing. In another aspect, the elapsed time interval between cell lysing and lysate encapsulation may be on the order of seconds. In yet another aspect, completion of RT-qPCR may occur on the order of about one hour.

In some embodiments, the present system and method may be applied to basic biomedical research, clinical applications, assessment of population-level heterogeneity in gene expression levels in normal or tumor cells with single-cell resolution and the like. In other embodiments, the present system and method may provide increased throughput with respect to the number of genes that may be quantified simultaneously. In still other embodiments, the present system and method may provide a highly multiplexed platform capable of detecting dozens of mRNA sequences for each initial droplet eluted from a given sample. This multiplexed platform may allow end-users to select cells located on the surface of the live tissue for downstream analysis and then lyse and analyze those cells at particular time points while retaining spatial information with respect to the tissue.

In some embodiments, one or more automation techniques may be applied to a SQUIRT-PCR system and method. For example, automation may be provided to harvest single-cell contents into single-wells of standard microtiter plates. The microtiter plates with single-cell lysates may be used by any downstream instrument for analysis of DNA, RNA, protein, small molecules, or combinations thereof. In one aspect, high-throughput quantitative mRNA profiling may be performed by harvesting single cell mRNA and interfacing a SQUIRT-PCR system with a high-throughput analytical platform. In one aspect, a high-throughput analytical platform may include thermal cycling and fluorescence detection capabilities. One example platform includes the BIOMARK HD system from FLUIDIGM. Accordingly, the present disclosure may provide an understanding of cellular heterogeneity in live intact tissue.

Figure 8:
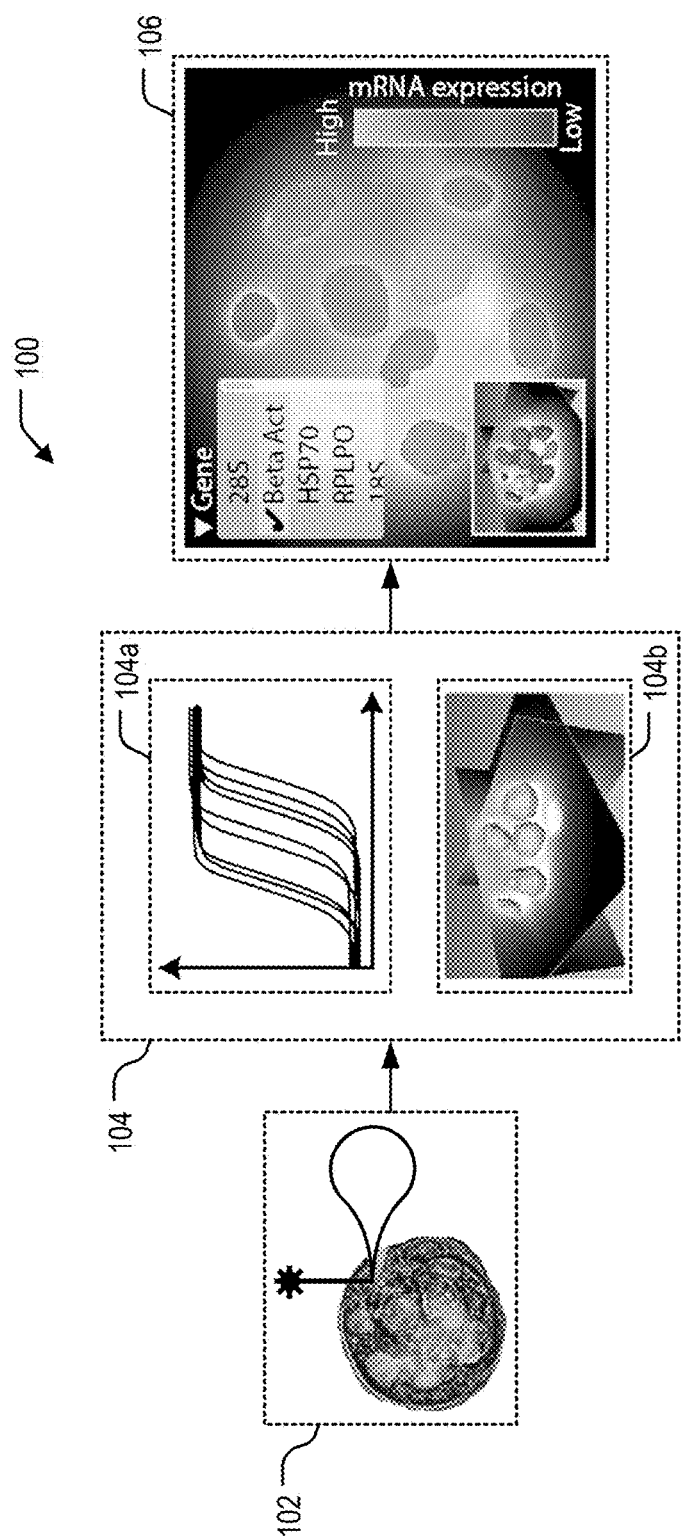
FIG. 8 is a schematic illustration of the principle of the SQUIRT-PCR system.

In some embodiments, SQUIRT-PCR system 100 may be used to construct a 3D map of mRNA expression in living tissue samples of up to 96 genes as shown in FIG. 8. In a first step 102, an ultrafast (pulsed) laser may lyse a cell-of-interest in a living tissue such as with a two-photon process. In a next step 104, the system 100 may collect the intracellular contents of the tissue sample and in a sub-step 104a, perform highly multiplexed RT-qPCR, while in a sub-step 104b, the system 100 may perform 3D image segmentation to reconstruct a 3D spatial map of mRNA expression with a large number of genes in a next step 106. The SQUIRT-PCR system 100 may automatically dispense single cell lysates into a standard microtiter plate format. As such, a user may use a SQUIRT-PCR system to analyze intracellular analytes of interest using one or more analytical platforms at the single-cell level in situ. Example applications where SQUIRT-PCR may be applied include epigenomics, RNA-seq, enzyme activity assays, mass spectroscopy, and the like.

In some embodiments, a system 108 may include an ultrafast laser system with a motorized fluorescence microscope as shown in FIG. 9. A plastic microfluidic cassette 110 may include a microfabricated cage 112 to retain a selected tissue sample 114 introduced into a straight microfluidic channel 116. During lysis, the system 108 may collect and automatically dispense single cell lysates 118 into individual wells 120 of a 96-well plate 122. After the reverse transcription reaction that converts mRNA to cDNA, and cDNA pre-amplification using a standard protocol, an integrated analytical platform may be used to analyze expression levels of 96 genes per cell for all lysed cells (i.e., 96 genes×96 cells). In one example, the integrated platform may integrate with a multi-well plate 124 including an integrated fluidics circuit 126 as shown in FIG. 10. Further, 3D image processing and visualization software (3D-SC) may be developed and used to correlate single-cell gene expression profiles with the 3D spatial locations of the corresponding cells within the cluster, as shown in FIG. 8. In another example, the device shown in FIG. 10 may be substituted for (or augmented with) one or more devices for epigenomic analysis, proteomic analysis, and the like.

In one aspect, the inventors have discovered that the cell disruption with a two-photon laser may be achieved with sub-micron resolution. Cell lysis may be well localized to the single-cell level. The cells next to the targeted cell may not be damaged in the lysis process. Combined with the image of the clusters, the acquired mRNA expression result may be tagged with spatial information of each lysed cells, thus generating a 3D map of mRNA expression.

In another aspect, the inventors have discovered that SQUIRT-PCR may be used to collect the contents of a single cell. The extracted mRNA may be preamplified, and then analyzed using qPCR. The sensitivity may be comparable with conventional single cell RT-qPCR where the housekeeping genes are obviously measurable. As expected, genes having lower relative expression levels are observed to have larger variations in expression level measurements.

In yet another aspect, the inventors have discovered that a SQUIRT-PCR system may be used to collect the lysate of 10 cells in about 200-cell cluster having a diameter of about 100 microns to about 150 microns without apparent carry-over contamination. A FLUIDIGM BioMark HD FLEXsix platform (12×12 qPCR array, capable of analyzing 12 genes for 12 individual single cells) yielded a sparse 3D map of mRNA expression of 12 genes. The entire process may be semi-automated and may be accomplished in about 30 minutes.

The schematic flow chart shown in FIG. 7 is generally set forth as a logical flow chart diagram. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in FIG. 7 are provided to explain the logical steps of the method and are understood not to limit the scope of the method. Although various arrow types and line types may be employed, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

EXAMPLES

For optimization of SQUIRT-PCR, two-photon (2P) laser lysis was demonstrated to effectively lyse individual cells with sub-cellular resolution in a cluster without incurring visible damage to the neighboring cells. Various laser settings were tested to achieve sufficient lysis performance and mRNA harvest efficiency. Laser settings and optical configurations found to yield efficient lysis included 100×1.3 NA oil-immersion objective lens, fundamental laser wavelength of 800 nm with a pulse duration of 150-200 fs, 250 kHz repetition rate, 0.4 µJ pulse energy, and ~1 s total exposure time. Moreover, targeting the nuclear membrane was discovered to easily generate micrometer-scale intracellular cavitation bubbles (Quinto-Su P A, et al. 2008, Lab Chip 8: 408-414; Li H, Sims C E, et al. 2001, Anal Chem 73: 4625-4631), which cause ruptures in the cell plasma membrane and the release of cell contents from the cell. Cavitation bubbles only existed for ~100 ms then dissipated. The 2P excitation was confirmed to induce the most efficient lysis when focused on the nucleus rather than anywhere else in the cell. Using a 100 ms-long series of pulses (25,000 pulses per series) targeted at the nuclear envelope, the lysis of the target cells and the release of their contents was accurately controlled. A study was performed with a 3D esophageal cell model using a laboratory (CBDA) established protocol. To visualize individual nuclei in cell clusters, cells were stained with the nuclear stain, Hoechst prior to 2PLL. FIGS. 11A-11C illustrate four points at the nuclear envelope region targeted by the focused laser beam and the resulting release of cellular contents visualized by the disappearance of fluorescence signal from the entire cell. FIGS. 12A-12C show a 3D cell cluster containing two cell populations including GFP-positive and GFP-negative cells (FIG. 12A). The cell cluster was injected into the microfluidic chip and was effectively retained in a microfabricated cage. GFP-positive cells were sequentially lysed and the release of the cell contents was monitored by the decrease in the GFP fluorescence signal (FIGS. 12B and 12C). The results showed that although the two GFP-positive cells were next to each other, the 2P laser precisely targeted and lysed each cell without affecting the other cell, as indicated by the release of the cytosolic green fluorescence protein from the individual cells. In addition, the Hoechst-labeled nuclei facilitate identifying the locations and areas of cell nuclei in 3D clusters. Microscopy analysis showed that 40 minute staining duration prior to lysis was sufficient for Hoechst to efficiently stain clusters with a diameter of 100-150 µm. The photobleaching of Hoechst stain does not pose a problem for cell visualization during the projected 15-minute process duration.

For mRNA expression analysis, 2PLL was demonstrated to serially lyse individual cells in tissue samples in a single microfluidic device. Conditions were identified for minimizing cell-cell contamination by extensively washing tissue samples between cell lysis cycles (FIG. 13). Single-cell mRNA yield from 2PLL was sufficient for detection with the FLUIDIGM BioMark platform. In addition, tests were performed to determine whether 2PLL induces cellular stress by monitoring heat shock protein 70 (HSP70) mRNA levels following multiple cell lysis cycles. Results indicated that while the HSP70 transcript level was detectable in the cell lysates, it was consistently low in all the cells (FIG. 13), which indicated that 2PLL does not induce detectable cellular stress during the 15-minute collection time.

A microfluidic cassette 128 capable of immobilizing cell clusters was constructed as shown in FIG. 14. Polydimethylsiloxane (PDMS), a biocompatible material widely used for lab-on-a-chip applications, was selected for the fabrication of the 1"×1" cassette 128. The width and height of the channel 132 are 500 µm and 100 µm, respectively. When a tissue sample (e.g., a cell cluster) is introduced into the channel 132, it is trapped in a microfabricated "cage" 130 in the middle of the channel 132 (FIGS. 15A-15D) by fluid flow as shown in FIG. 16. Various designs for cage 130 were tested with different post geometries and the gaps between posts varying from 15 µm to 30 µm. The bottom of the cassette 128 was a standard 170 µm-thick cover glass, so it is compatible with imaging using high numerical aperture (NA) objective lenses. Testing determined that a loaded cell cluster can be held still in the cage 130 with a small flow rate (<1 µL/min), whereas it remains viable and intact with only insignificant deformation when the flow rate exceeds 300 µL/min as shown in FIG. 16. The surface of the channel 132 was coated with polyethylene glycol (PEG) to avoid surface adsorption of the molecules in the lysate. In general, it may be useful to load only one tissue structure into the cassette 128 at a time.

A robotic tissue loading platform with visual feedback was implemented to pick an individual cell cluster from a large population of clusters, and to transfer it to the microfluidic cassette for 2PLL. This platform is based on a single-cell loading platform (Anis Y H, et al. 2010, IEEE Transactions on Automation Science and Engineering 7: 598-606; Anis Y, et al. 2011, Biomedical Microdevices 13: 651-659). Before tissue loading, the user may insert the microfluidic cassette into the loading head. The user may use a microscope on the platform to identify a tissue sample of interest, then use the loading head on a robotic arm to automatically aspirate it into the microfluidic cassette and load it into the microfabricated cage as shown in FIGS. 17A-17C. A camera on the loading head allows the user to visually confirm that the tissue is trapped in the cage. According to one method, the loading process requires relatively minimal effort and takes less than about 5 minutes. Once loading is completed, the user may transfer the cassette from the loading head to the 2PLL station for laser lysis.

In one aspect, adhesion of RNA to PDMS may be a concern during the collection of lysate due to the small expected concentrations in single cells. To test the ability of a PEG (polyethylene glycol) surface treatment to mitigate adhesion, a PEG coated microfluidic chip was compared experimentally to an uncoated one. Both chips were injected with the control mRNA, RBCL (ribulose-bisphosphate carboxylase), the RNA sample was allowed to flow through the chip, and the flow through was collected onto the 96-well plate. The amount of RBCL absorbed by the microfluidic channels was tested by determining RBCL RNA levels collected from the outlet before and after the introduction of the RNA sample into the microfluidic channels as shown in FIGS. 18A-18C. Since PDMS has the propensity to bind RNA, the untreated microfluidic chip was predicted to absorb significant amount of RBCL. In contrast, minimal binding of RBCL to the PEG treated channel was anticipated since PEG has previously been shown to block RNA from binding PDMS (Yamanaka K, et al. 2011, The Analyst 136: 2064; Zhou J, et al. 2010, ELECTROPHORESIS 31: 2-16). Results showed that the PEG treated channel had significantly higher RBCL RNA levels during the entire time when RBCL passed through the channel as shown in FIG. 18C, confirming the notion that PEG coated PDMS channels can minimize RNA absorption.

The present invention has been described in terms of one or more preferred embodiments, and it should be appreciated that many equivalents, alternatives, variations, and modifications, aside from those expressly stated, are possible and within the scope of the invention.

Each reference identified in the present application is herein incorporated by reference in its entirety.

While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

We claim:

1. A method for three-dimensional spatial mapping of a target molecule expression in a cell in a multicellular environment without disaggregation of said cell from said multicellular environment, comprising:
    (1) lysing a first cell of interest from an imaged cluster of cells with a laser, wherein said cluster of cells is located in a containment device configured for flow through of lysate;
    (2) collecting cellular contents of the lysed cell from said containment device by flowing said lysate to an outlet;
    (3) performing RT-qPCR on said cellular contents of the lysed cell;
    (4) repeating steps (1)-(3) with a second cell of interest from said cluster of cells; and
    (5) constructing a 3D spatial map of said target molecule expression in said first and second cells based on a RT-qPCR result on a respective content of each lysed cell and known coordinates of each cell determined from said imaged cluster of cells.

2. The method of claim 1, wherein said target molecule of interest is selected from the group consisting of DNA, RNA, and protein.

3. The method of claim 1, wherein said performing RT-qPCR utilizes SQUIRT-PCR.

4. The method of claim 1, wherein said lysing utilizes a two-photon (2P) process.

5. The method of claim 1, wherein the cell is live, fixed, frozen or preserved.

* * * * *